(12) United States Patent
Fukuoka et al.

(10) Patent No.: US 7,485,705 B2
(45) Date of Patent: Feb. 3, 2009

(54) WATER-SOLUBLE TETRAZOLIUM COMPOUNDS

(75) Inventors: Yuriko Fukuoka, Kumamoto (JP); Ryo Sakamoto, Kumamoto (JP); Munetaka Ishiyama, Olney, MD (US)

(73) Assignee: Dojindo Laboratories, Kumamoto (JP)

( * ) Notice: Subject to any disclaimer, the term of this patent is extended or adjusted under 35 U.S.C. 154(b) by 395 days.

(21) Appl. No.: 10/563,702

(22) PCT Filed: Jul. 13, 2004

(86) PCT No.: PCT/JP2004/009953

§ 371 (c)(1),
(2), (4) Date: Jan. 5, 2006

(87) PCT Pub. No.: WO2005/023786

PCT Pub. Date: Mar. 17, 2005

(65) Prior Publication Data

US 2007/0111274 A1    May 17, 2007

(30) Foreign Application Priority Data

Jul. 14, 2003    (JP)    ............................. 2003-273982

(51) Int. Cl.
C09B 44/08    (2006.01)
C12Q 1/26    (2006.01)
C12Q 1/32    (2006.01)

(52) U.S. Cl. .............................. 534/605; 435/25; 435/26

(58) Field of Classification Search ................ 534/605, 534/574; 435/25, 26; 514/381; 548/250
See application file for complete search history.

(56) References Cited

U.S. PATENT DOCUMENTS 6,913,878 B2 *    7/2005    Nakamura et al. ............. 435/4

* cited by examiner

Primary Examiner—Kamal A Saeed
Assistant Examiner—Kristin Bianchi
(74) Attorney, Agent, or Firm—Fay Sharpe LLP

(57) ABSTRACT

The purpose of the present invention is to provide a water-soluble tetrazolium compound that will form a water-soluble formazan exhibiting long-wavelength absorption and is stable in aqueous solution for a long period and suitable for the quantitative analysis of dehydrogenases or substrates thereof. Disclosed is a water soluble tetrazolium compound expressed by the following general formula (1):

wherein each of $R^1$ to $R^{19}$ independently represents hydrogen atom; nitro group; sulfonate group or alkyl, alkoxy, sulfoalkyl or sulfoalkyloxy groups having 1 to 4 carbon atoms; provided that each of at least two of $R^1$ to $R^{19}$ independently represents sulfonate group; or sulfoalkyl or sulfoalkyloxy groups having 1 to 4 carbon atoms; and M represents an alkali metal or ammonium ion.

4 Claims, 7 Drawing Sheets

WATER-SOLUBLE TETRAZOLIUM COMPOUNDS

TECHNICAL FIELD

The present invention relates to tetrazolium compounds and more particularly relates to novel water-soluble tetrazolium compounds that are suitable for a quantitative analysis of dehydrogenases or substrates thereof.

BACKGROUND ART

Tetrazolium compounds (tetrazolium salts) have been utilized for the quantitative analysis of dehydrogenases such as lactate dehydrogenase (hereinafter abbreviated to "LDH"), alcohol dehydrogenase and glutamate dehydrogenase. This is because a tetrazolium compound receives a hydrogen liberated by the action of a dehydrogenase, among various types as mentioned above, via an intermediate electron carrier to form a formazan, in which the measurement of the absorbance of the resultant formazan enables the quantitative analysis of the dehydrogenase or the substrate thereof.

Among these dehydrogenases, in particular, LDH is distributed in all somatic cells, and abundantly exists particularly in myocardia, liver and skeletal muscles and it is known that serum LDH activity markedly increases in patients with diseases such as cardiac infarction, malignant tumor, hepatic disease, progressive muscular atrophy, intravascular hemolysis and megaloblastic anemia. Therefore, measurement of LDH activity in blood provides meaningful information for clinical diagnosis. There is also desired a method based on dehydrogenases that experience little interference from biological materials, for measurements of uric acid and bile acid in blood.

Determination of cell proliferations and cytotoxicities has recently been made possible by using dehydrogenase activity in cultured cells or leaked out of cells, as an index, and the method is widely utilized as a convenient measure to learn the toxicities of chemicals and the efficacies of newly developed therapeutic products.

As the hydrogen receptors for the above-mentioned purposes, there have been generally utilized such materials as 3,3'-[3,3'-dimethoxy-(1,1'-biphenyl)-4,4'-diyl]-bis-[2-(4-nitrophenyl)-5-2H tetrazolium chloride] (hereinafter abbreviated to "nitro-TB") and [3-(4,5-dimethylthiazol-2-yl)-2,5-diphenyltetrazolium bromide] (hereinafter abbreviated to "MTT").

Formazan formed from nitro-TB or MTT upon receiving hydrogen is, however, insoluble in water and inconvenient for use. A drawback encountered particularly in the application of these compounds to the automated analysis or microplate analysis is that the formazan formed stains the detection system such as cell, tubes and microplate. The use of a tetrazolium salt that will form a water-soluble formazan is therefore required to eliminate the drawback. Especially, in measuring a biological sample, a purple to blue formazan with absorption at a longer wavelength is desired so as to avoid interference with the color of biological material which may be included in the sample.

The research group to which the present inventors belong previously developed tetrazolium compounds that fulfill these requirements (JP-B-2592436, JP-B-2819258 and JP-B-2995880). While the tetrazolium compounds disclosed in these patents serve as reagents that are practically applicable to automated or microplate analysis of dehydrogenases and the substrates thereof, more improvement is needed. In particular, the water-soluble tetrazolium compounds proposed so far that form the formazans with long-wavelength absorption are unstable in aqueous solution, which makes long-term storage as reagents difficult.

DISCLOSURE OF THE INVENTION

Problems to be Resolved by the Invention

The purpose of the present invention is to provide a water-soluble tetrazolium compound that will form a water-soluble formazan exhibiting long-wavelength absorption and is stable in an aqueous solution for a long period and suitable for the quantitative analysis of dehydrogenases or substrates thereof.

Means of Solving The Problems

Through extensive studies on the compounds that will form highly soluble formazans therefrom and that have a high stability, the present inventors succeeded in synthesizing novel water-soluble tetrazolium compounds and found that the compounds are excellent hydrogen receptors and the formazans formed therefrom are water-soluble, stable and applicable to the measurement of dehydrogenases and the substrates thereof without suffering from the staining onto the analytical instrument or precipitation.

Thus, according to the present invention, there is provided a tetrazolium compound expressed by the following general formula (1):

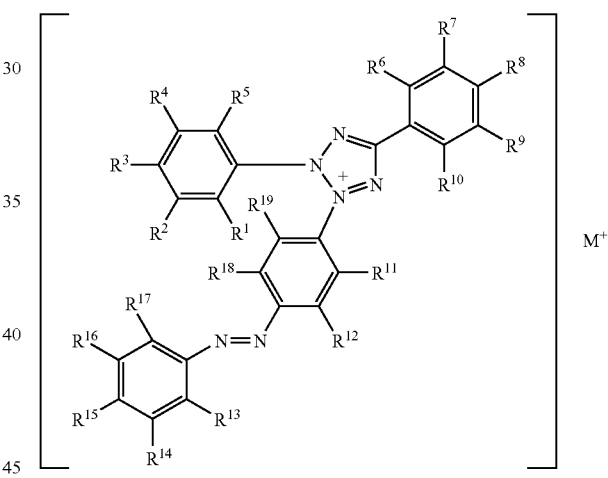

wherein each of $R^1$ to $R^{19}$ independently represents hydrogen atom; nitro group; sulfonate group; or alkyl, alkoxy, sulfoalkyl or sulfoalkyloxy groups having 1 to 4 carbon atoms; provided that each of at least two of $R^1$ to $R^{19}$ represents sulfonate group; or sulfoalkyl or sulfoalkyloxy groups having 1 to 4 carbon atoms; and M represents an alkali metal or ammonium ion.

In addition, the present invention provides a process for a quantitative analysis of a dehydrogenase or substrate thereof in which the above-mentioned tetrazolium compound is utilized. The process may include the measurement of the activity of the dehydrogenase present in cultured cells or leaked out of cells.

Advantageous Effects of the Invention

A water-soluble tetrazolium compound of the present invention produces a formazan with enhanced solubility and enables sensitive determination of a dehydrogenase and the substrate thereof with automated or microplate analysis without causing undesirable staining of the analytical instrument.

Moreover, the tetrazolium compounds of the present invention have excellent storage stability as reagents because they are stable in an aqueous solution for a long period.

BEST MODE FOR CARRYING OUT THE INVENTION

The compounds of the present invention expressed by the general formula (1) can be synthesized by utilizing reactions known in the art in the usual manner. For example, a phenylhydrazine expressed by the general formula (2)

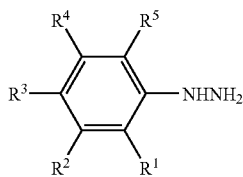

(2)

is rendered to react with an aldehyde, compound in an alcohol solvent to produce a hydrazon expressed by the general formula (3),

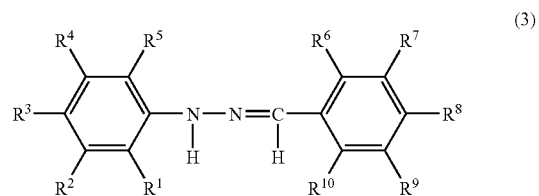

(3)

followed by the reaction of the corresponding diazonium salt in an aqueous solution under a basic condition, thereby producing a formazan expressed by the general formula (4).

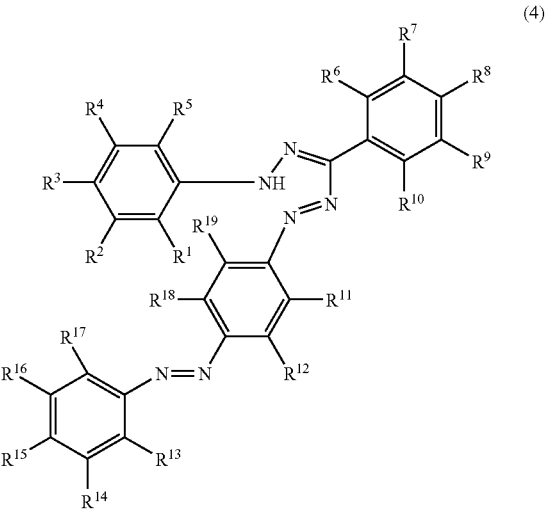

(4)

wherein a base such as sodium hydroxide or potassium hydroxide is used.

The formazan of the general formula (4) is oxidized with an oxidizing agent such as butyl nitrite or sodium hypochlorite in an alcohol solvent to produce a tetrazolium compound of the general formula (1).

Figure 1:
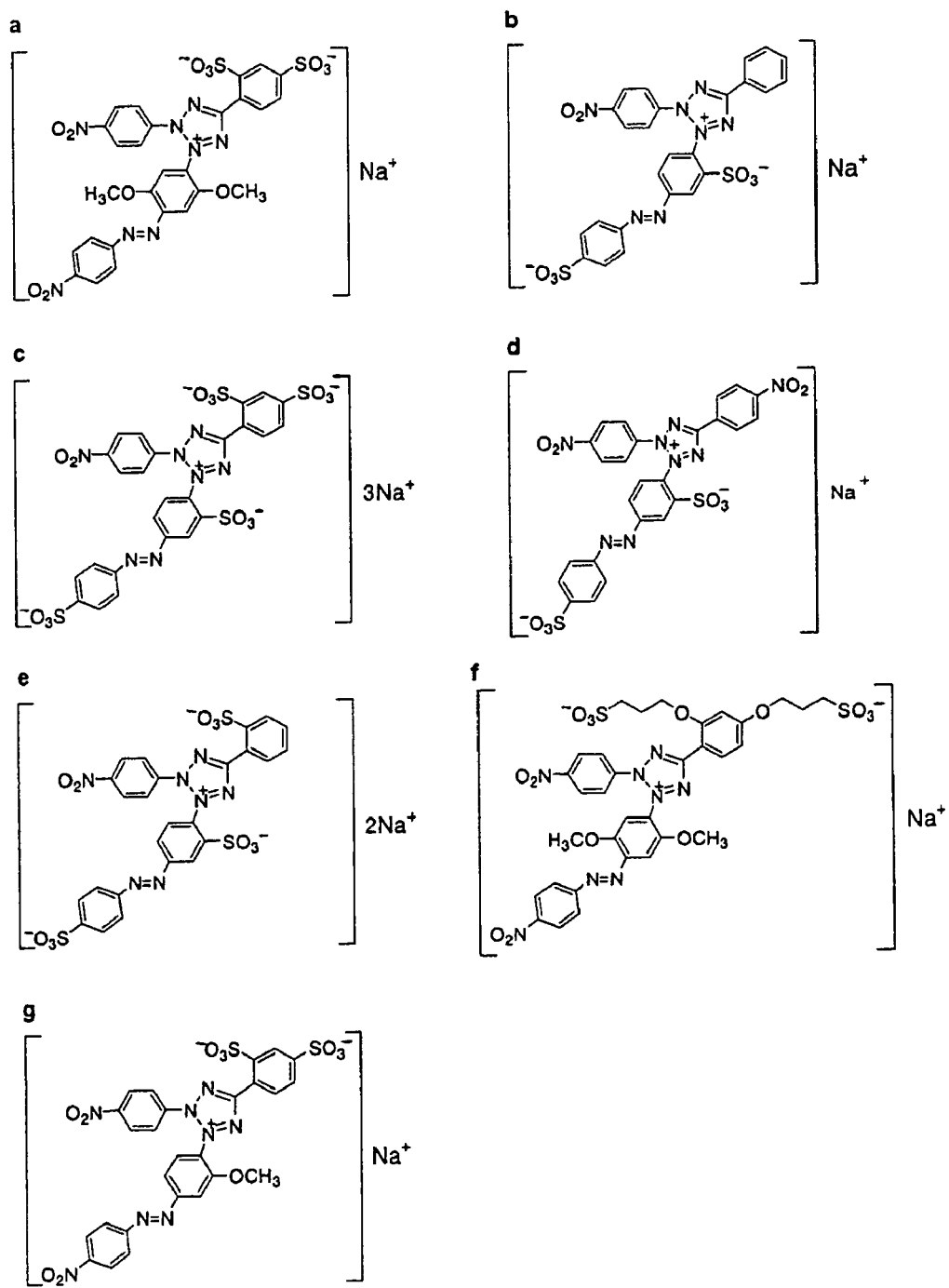
FIG. 1 exemplifies the chemical structure formulae of the tetrazolium compounds of the present invention.

While as specific examples of the tetrazolium compounds of the present invention thus synthesized, FIG. 1 shows the chemical structures of the tetrazolium compounds utilized in the examples described later, the tetrazolium compounds of the present invention are not limited to these examples. As is clear from FIG. 1, these compounds represent the compoundsof general formula (1) wherein $R^1$, $R^2$, $R^4$, $R^5$, $R^7$, $R^9$, $R^{10}$, $R^{12}$, $R^{13}$, $R^{14}$, $R^{16}$, $R^{17}$ and $R^{19}$ are hydrogen atoms, $R^3$ is nitro group, $R^6$ and $R^8$ are sulfonic acid groups, $R^{11}$ and $R^{18}$ are methoxy groups (compound a); $R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{16}$, $R^{17}$, $R^{18}$ and $R^{19}$ are hydrogen atoms, $R^3$ is nitro group, $R^{11}$ and $R^{15}$ are sulfonic acid groups (compound b); $R^1$, $R^2$, $R^4$, $R^5$, $R^7$, $R^9$, $R^{10}$, $R^{12}$, $R^{13}$, $R^{14}$, $R^{16}$, $R^{17}$, $R^{18}$ and $R^{19}$ are hydrogen atoms, $R^3$ is nitro group, $R^6$, $R^8$ and $R^{15}$ are sulfonic acid groups (compound c); $R^1$, $R^2$, $R^4$, $R^5$, $R^6$, $R^7$, $R^9$, $R^{10}$, $R^{12}$, $R^{13}$, $R^{14}$, $R^{16}$, $R^{17}$, and $R^{19}$ are hydrogen atoms, $R^3$ and $R^8$ are nitro groups, $R^{11}$ and $R^{15}$ are sulfonic acid groups (compound d); $R^1$, $R^2$, $R^4$, $R^5$, $R^7$, $R^8$, $R^9$, $R^{10}$, $R^{12}$, $R^{13}$, $R^{14}$, $R^{16}$, $R^{17}$, $R^{18}$ and $R^{19}$ are hydrogen atoms, $R^3$ is nitro group, $R^6$, $R^{11}$ and $R^{15}$ are sulfonic acid groups (compound e); $R^1$, $R^2$, $R^4$, $R^5$, $R^7$, $R^9$, $R^{10}$, $R^{12}$, $R^{13}$, $R^{14}$, $R^{16}$, $R^{17}$ and $R^{19}$ are hydrogen atoms, $R^3$ is nitro group, $R^6$ and $R^8$ are sulfoalkyloxy groups, $R^{11}$ and $R^{18}$ are methoxy groups (compound f); and $R^1$, $R^2$, $R^4$, $R^5$, $R^7$, $R^9$, $R^{10}$, $R^{12}$, $R^{13}$, $R^{14}$, $R^{16}$, $R^{17}$, and $R^{19}$ are hydrogen atoms, $R^3$ is nitro group, $R^6$, $R^8$, $R^{11}$ and $R^{15}$ are sulfonic acid groups (compound g).

The formazans formed from the water-soluble tetrazolium compounds of the present invention absorb light at a long wavelength region and have a unique absorption maximum wavelength for each tetrazolium compound. For example, the formazans formed from the above-mentioned compounds a to g have the absorption maximum wavelengths shown in Table 1, respectively. In addition, the tetrazolium compounds of the present invention are extremely stable in water and do not decompose with time.

TABLE 1

| Compounds | Absorption maximum wavelength |
|---|---|
| a | 527 nm |
| b | 493 nm |
| c | 472 nm |
| d | 530 nm |
| e | 474 nm |
| f | 530 nm |
| g | 437 nm |

Hereinafter, examples of the present invention will be described to illustrate the features of the present invention more specifically. However, the scope of the invention is not limited to these examples.

Example 1 exemplifies the synthesis of the water-soluble tetrazolium compounds of the present invention. Example 2 demonstrates that the water-soluble tetrazolium compounds of the present invention are stable and do not decompose with time. Example 3 shows that the absorbance of the formazans formed from the water-soluble tetrazolium compounds of the present invention correlates with the concentration of NADH in 1-methoxy-PMS/NADH system, as a model of the dehydrogenase reaction, demonstrating that the water-soluble tetrazolium compounds of the present invention are applicable to the quantitative analysis of the dehydrogenases and the substrates thereof. Example 4 shows that the absorbance of the formazans formed from the tetrazolium compounds of the present invention correlates with the number of cells in 1-methoxy-PMS/cultured cells system, demonstrating that the water-soluble tetrazolium compounds of the present invention are applicable to the quantitative analysis of the dehydrogenases and the substrates thereof in cultured cell systems.

EXAMPLE 1

(Synthesis of Compound a)

p-Nitrophenyl hydrazine (10 g, 65.3 mmol) and disodium 4-formyl-1,3-benzene-disulfonate monohydrate (20.26 g, 65.3 mmol) were suspended in 300 ml of methanol and the mixture was heated and refluxed for 2 hours. After cooling the reaction suspension, the precipitate of the suspension was collected by filtration, producing hydrazone compound (25.3 g, yield 86.9%).

The hydrazone compound thus obtained (7.61 g, 17.1 mmol) was dissolved in a solvent mixture of tetrahydrofuran (200 ml) and water (200 ml) and cooled to 3° C. To the aqueous solution of the hydrazone compound, was added 2,5-dimethoxy-4-(4-nitrophenylazo)benzene diazonium salt ½ zinc chloride. The solution of sodium hydroxide (2.08 g) in water (40 ml) was added dropwise to the reaction solution while keeping the temperature at 0 to 3° C. and the solution was stirred for 6 hours after the addition was completed. Hydrochloric acid was added to the reaction mixture to make it slightly acidic. Then the solvent mixture of tetrahydrofuran and water was distilled away under reduced pressure. The crude product thus obtained was purified by reprecipitation from water/alcohol, producing 1.5 g (11% yield) of formazan.

The formazan thus obtained (0.46 g, 0.61 mmol) was dissolved in methanol (20 ml). After adding hydrochloric acid (0.5 ml, 4.9 mmol) to the formazan solution, butyl nitrite (1 g, 9.1 mmol) was added and the mixture was stirred at room temperature for one hour. After the methanol solvent was distilled off under reduced pressure, the resultant crude product was purified by reprecipitation from water/alcohol, producing 30 mg (6.7% yield) of tetrazolium compound a of general formula (1).

Proton nuclear magnetic resonance (hereinafter abbreviated to "$^1$H-NMR"): ($D_2O$, 300 MHz) δ 3.64 (3H, s, —$OCH_3$), 4.18 (3H, s, —$OCH_3$), 7.09-8.05 (4H, m, aromatic CH), 8.17-8.27 (4H, m, aromatic CH), 8.27-8.37 (2H, m, aromatic CH), 8.58-8.68 (3H, m, aromatic CH); Infrared spectroscopy (hereinafter abbreviated to "IR") (potassium bromide pellet; hereinafter abbreviated to "KBr"): 3460, 3100, 1610, 1525, 1500, 1345, 1230, 1118 $cm^{-1}$; Mass analysis (mass spectroscopy; hereinafter abbreviated to "MS") m/e 735 [M+1].

(Synthesis of Compound b)

Compound b was synthesized by a similar method to that of compound a.

$^1$H-NMR: (methanol-$d_4$, 300 MHz) δ 7.63-7.78 (3H, m, aromatic CH), 8.01-8.28 (4H, m, aromatic CH), 8.32-8.38 (2H, d, aromatic CH), 8.44-8.54 (3H, m, aromatic CH); IR (KBr): 3450, 3100, 1620, 1520, 1455, 1350, 1220, 1030, 850 $cm^{-1}$; MS: m/e 630 [M+1].

(Synthesis of Compound c)

Compound c was synthesized by a similar method to that of compound a.

$^1$H-NMR: (methanol-$d_4$, 300 MHz) δ 7.98-8.12 (5H, m, aromatic CH), 8.14-8.21 (1H, m, aromatic CH), 8.23-8.37 (3H, m, aromatic CH), 8.41-8.57 (4H, m, aromatic CH), 8.71-8.75 (1H, d, aromatic CH); IR (KBr): 3480, 3100, 1638, 1540, 1355, 1230, 1140, 855, 610 $cm^{-1}$; MS: m/e 834 [M+1].

(Synthesis of Compound d)

p-Nitrophenyl hydrazine (14 g, 91.4 mmol) and p-nitrobenzaldehyde (13.8 g, 91.4 mmol) was suspended in methanol (400 ml) and the mixture was heated and refluxed for 2 hours. After cooling the reaction suspension, the precipitate of the suspension was collected by filtration, producing hydrazone compound (23.6 g, yield 90.1%).

Disodium 4-amino-1,1'-azobenzene-3,4-disulfonate (31.2 g) was suspended in water (200 ml) and cooled below 5° C. To the suspension, conc. hydrochloric acid (25.7 ml) and sodium nitrite (5.67 g) in water (50 ml) were added and the mixture was stirred for one hour at 0-5° C., producing an aqueous solution of diazonium compound.

The hydrazone compound (7.61 g, 17.1 mmol) was dissolved in a solvent mixture of tetrahydrofuran (300 ml) and water (50 ml) and cooled to 3° C. To the aqueous solution of the hydrazone compound, the aqueous solution of the diazonium compound synthesized as stated above was added. A solution of sodium hydroxide (13.2 g) in water (160 ml) was added dropwise to the reaction solution while keeping the temperature at 0 to 3° C. and the solution was stirred for 3 hours after the addition was completed. Hydrochloric acid was added to the reaction mixture to make it slightly acidic. Then the solvent mixture of tetrahydrofuran and water was distilled off under reduced pressure. The crude product thus obtained was purified by reprecipitation from methanol/dimethylformamide, producing 52 g (90.6% yield) of diazonium salt.

The formazan thus obtained (3 g, 4.3 mmol) was dissolved in a solvent mixture of methanol (200 ml) and dimethylformamide (50 ml). After adding hydrochloric acid (9 ml, 0.11 mmol) to the formazan solution, an aqueous solution of sodium hypochlorite (20 ml) was added and the mixture stirred at room temperature for one hour. After the methanol-dimethylformamide solvent mixture was distilled off under reduced pressure, the crude product was purified by reprecipitation from water/alcohol, producing 0.8 g (27.6% yield) of the tetrazolium compound d of general formula (1).

$^1$H-NMR: (methanol-$d_4$, 300 MHz) δ 8.12-8.19 (3H, m, aromatic CH), 8.20-8.23 (1H, d, aromatic CH), 8.23-8.26 (1H, d, aromatic CH), 8.27 (1H, s, aromatic CH), 8.35-8.40 (2H, m, aromatic CH), 8.60-8.68 (5H, m, aromatic CH), 8.71 (1H, d, aromatic CH), 8.74 (1H, s, aromatic CH); IR (KBr): 3500, 3110, 1630, 1550, 1475, 1365, 1240, 1050, 870 $cm^{-1}$; MS: m/e 675 [M+1].

(Synthesis of Compound e)

Compound e was synthesized by a similar method to that of compound a and d. $^1$H-NMR: (methanol-$d_4$, 300 MHz) δ 7.98-8.12 (5H, m, aromatic CH), 8.14-8.21 (1H, m, aromatic CH), 8.23-8.37 (3H, m, aromatic CH), 8.41-8.57 (4H, m, aromatic CH), 8.71-8.75 (1H, d, aromatic CH); IR (KBr): 3480, 3100, 1638, 1540, 1355, 1230, 1140, 855, 610 $cm^{-1}$; MS: m/e 834 [M+1].

(Synthesis of Compound f)

Compound f was synthesized by a similar method to that of compound a and d. $^1$H-NMR: (methanol-$d_4$, 300 MHz) δ 2.22-2.48 (4H, m, —$CH_2$—), 3.10-3.28 (2H, m, —$CH_2$—), 3.66 (3H, s, —$OCH_3$), 4.21-4.30 (2H, m, —$CH_2$—), 6.66-6.68 (1H, m, aromatic CH), 6.89-6.93 (1H, m, aromatic CH), 6.89-6.93 (1H, m, aromatic CH), 7.41 (1H, s, aromatic CH), 7.70-7.75 (1H, m, aromatic CH), 7.91 (1H, s, aromatic CH), 8.12-8.22 (4H, m, aromatic CH), 8.42-8.48 (2H, m, aromatic CH), 8.52-8.58 (2H, m, aromatic CH); IR (KBr): 3475, 2950, 1620, 1510, 1350, 1210, 1050, 860, 610 $cm^{-1}$; MS: m/e 851 [M+1].

(Synthesis of Compound g)

Compound g was synthesized by a similar method to that of compound a and d. $^1$H-NMR: (methanol-$d_4$, 300 MHz) δ 7.53-7.63 (1H, m, aromatic CH), 7.96-8.01 (1H, s, aromatic CH), 8.09-8.26 (6H, m, aromatic CH), 8.28-8.42 (3H, m, aromatic CH), 8.52-8.64 (3H, m, aromatic CH); IR (KBr): 3450, 3100, 1600, 1530, 1350, 1230, 1040, 850, 610, 550 $cm^{-1}$; MS: m/e 705 [M+1].

EXAMPLE 2

Figure 2:
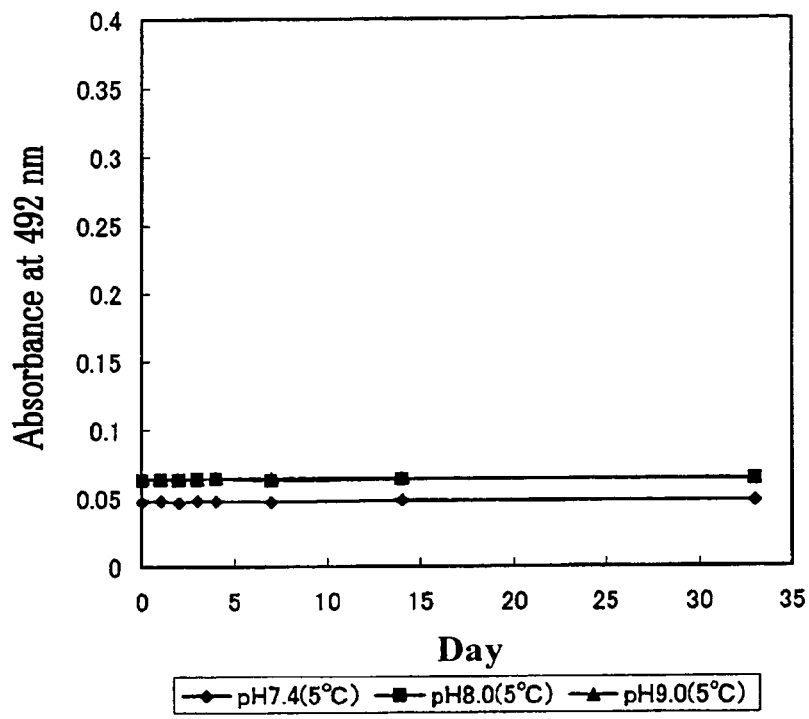
FIG. 2 graphically demonstrates the stability of the tetrazolium compound d of the present invention in a buffer solution (5° C.).
Figure 3:
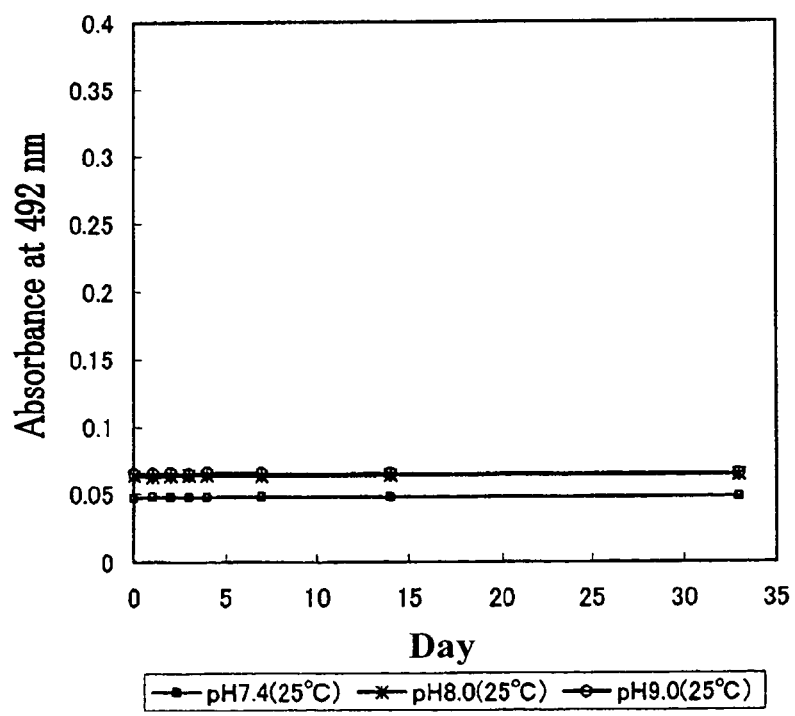
FIG. 3 graphically demonstrates the stability of the tetrazolium compound d of the present invention in a buffer solution (25° C.).
Figure 4:
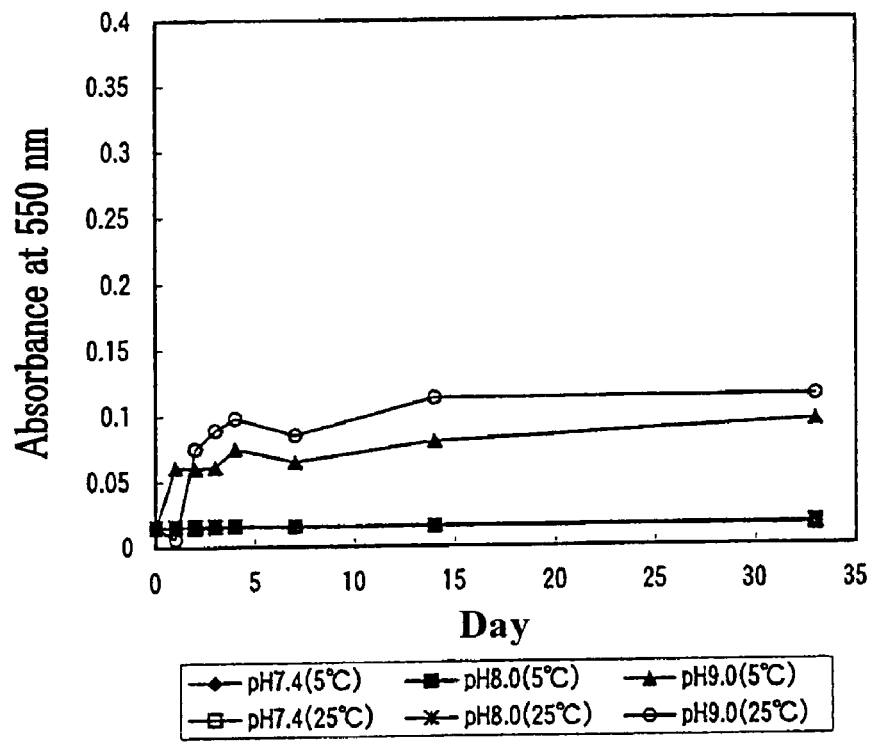
FIG. 4 graphically demonstrates the stability of the tetrazolium compound of prior art that is unstable in aqueous solution, for comparison.

Tris-HCl (50 mM) buffer solutions of compounds a, b, c, d, e, f and g were prepared so that the concentrations of the compounds were 1 mM. The solutions were stored at 4 or 25° C. and each compound was measured for the absorbance at the absorption maximum wavelengths of each formazan as shown in foregoing Table 1. The results with compound d are shown in FIGS. 2 and 3. Similar results were also obtained for other compounds. For all compounds no change was observed in the absorbance for 30 days after preparation, verifying that the compounds of the present invention are stable in aqueous solution without being decomposed to formazans. FIG. 4 shows the change of the absorption of water-soluble tetrazolium compound disclosed in JP-B-2995880 for comparison, from which it is understood that the compound is somewhat inferior in the stability with elapse of time.

EXAMPLE 3

Figure 5:
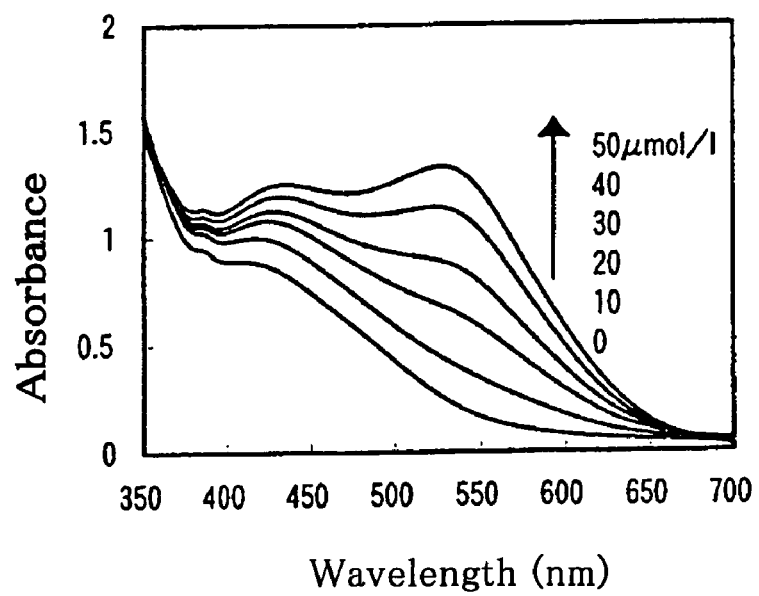
FIG. 5 shows the absorption spectra of the formazan formed from tetrazolium compound a of the present invention.
Figure 6:
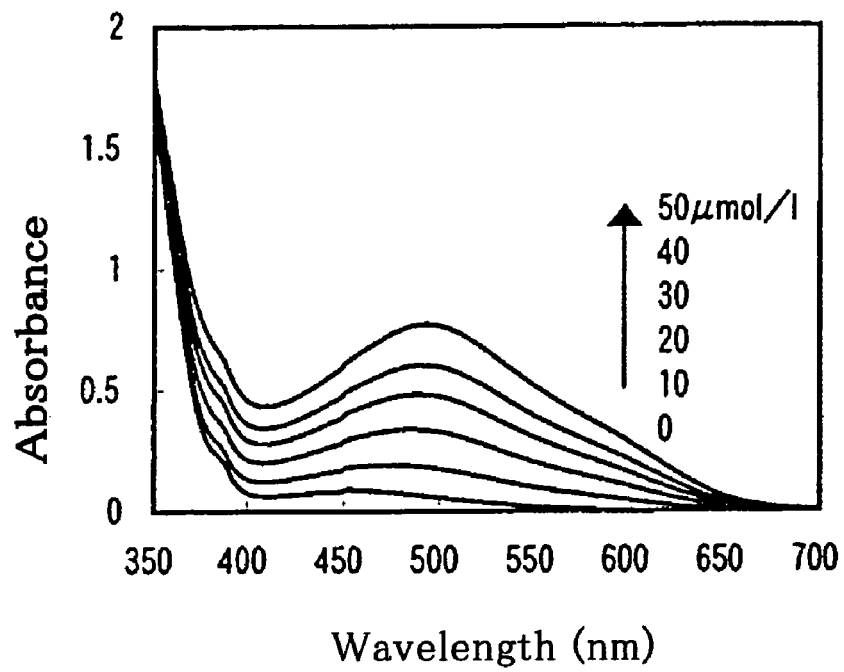
FIG. 6 shows the absorption spectra of the formazan formed from tetrazolium compound b of the present invention.
Figure 7:
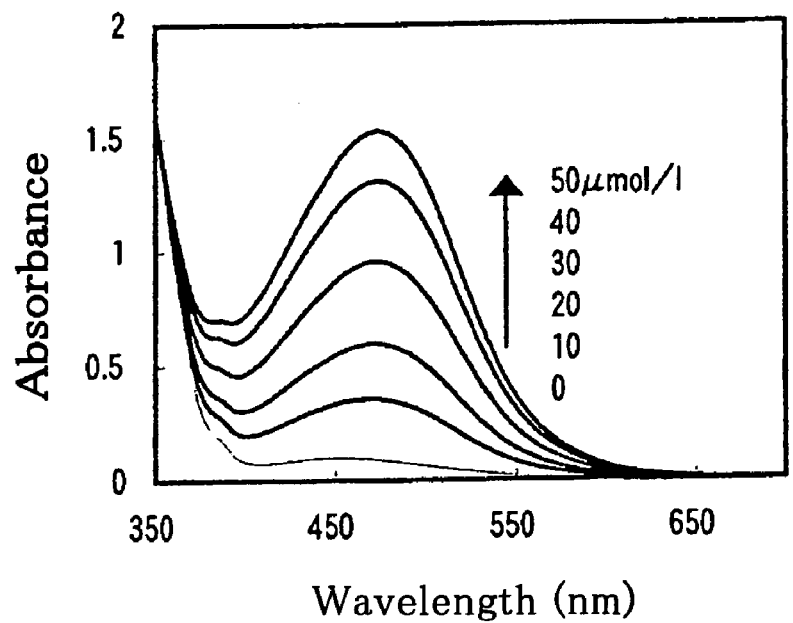
FIG. 7 shows the absorption spectra of the formazan formed from tetrazolium compound c of the present invention.
Figure 8:
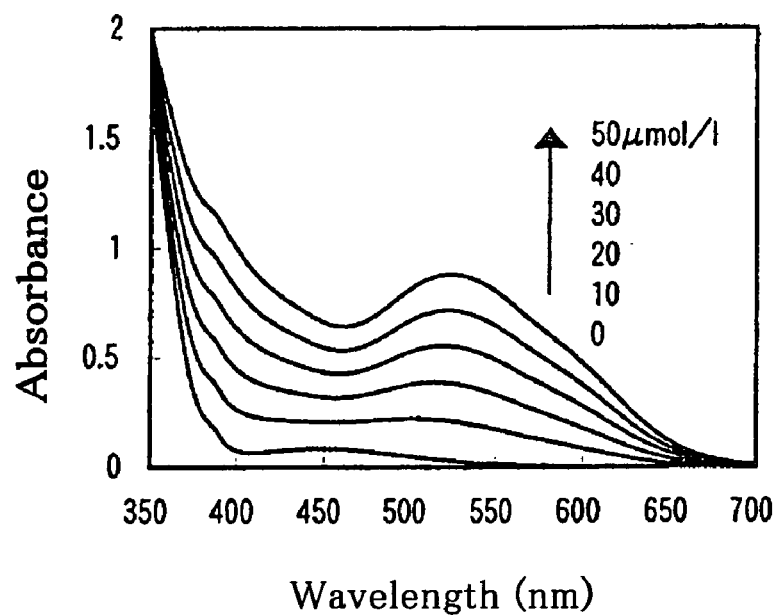
FIG. 8 shows the absorption spectra of the formazan formed from tetrazolium compound d of the present invention.
Figure 9:
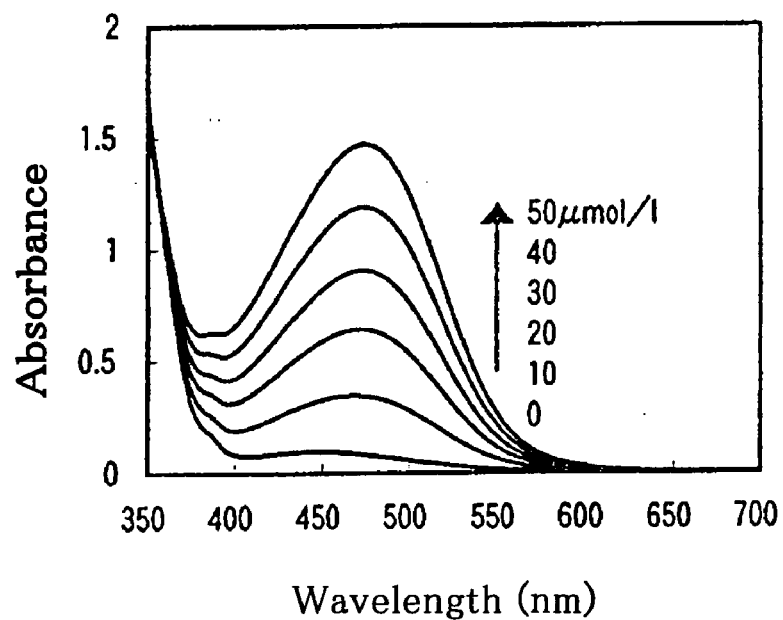
FIG. 9 shows the absorption spectra of the formazan formed from tetrazolium compound e of the present invention.
Figure 10:
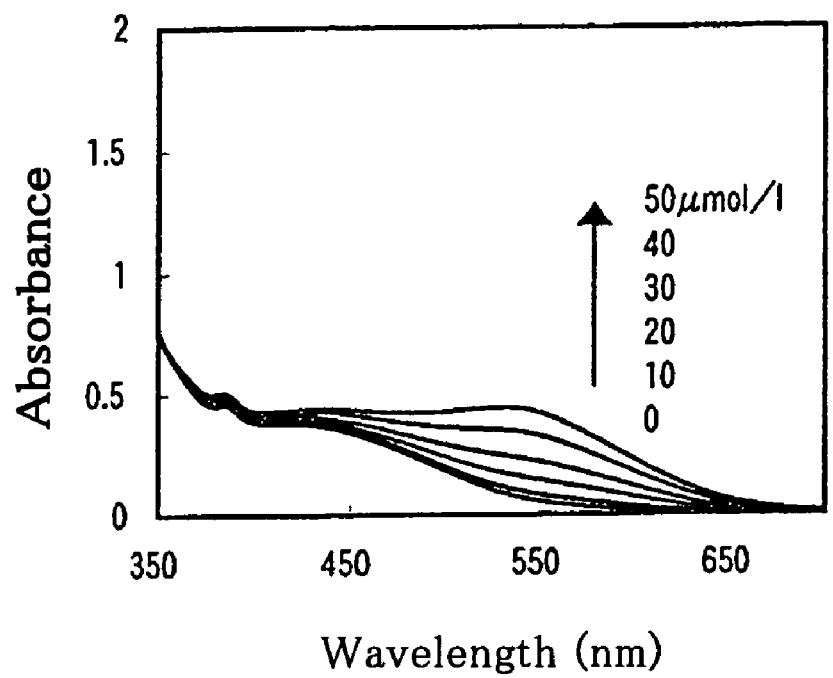
FIG. 10 shows the absorption spectra of the formazan formed from tetrazolium compound f of the present invention.
Figure 11:
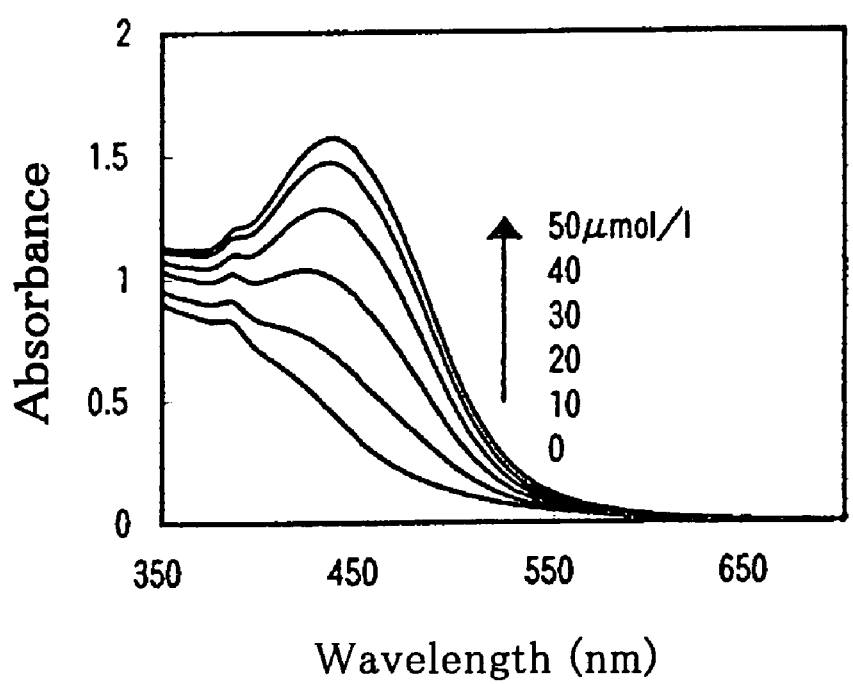
FIG. 11 shows the absorption spectra of the formazan formed from tetrazolium compound g of the present invention.
Figure 12:
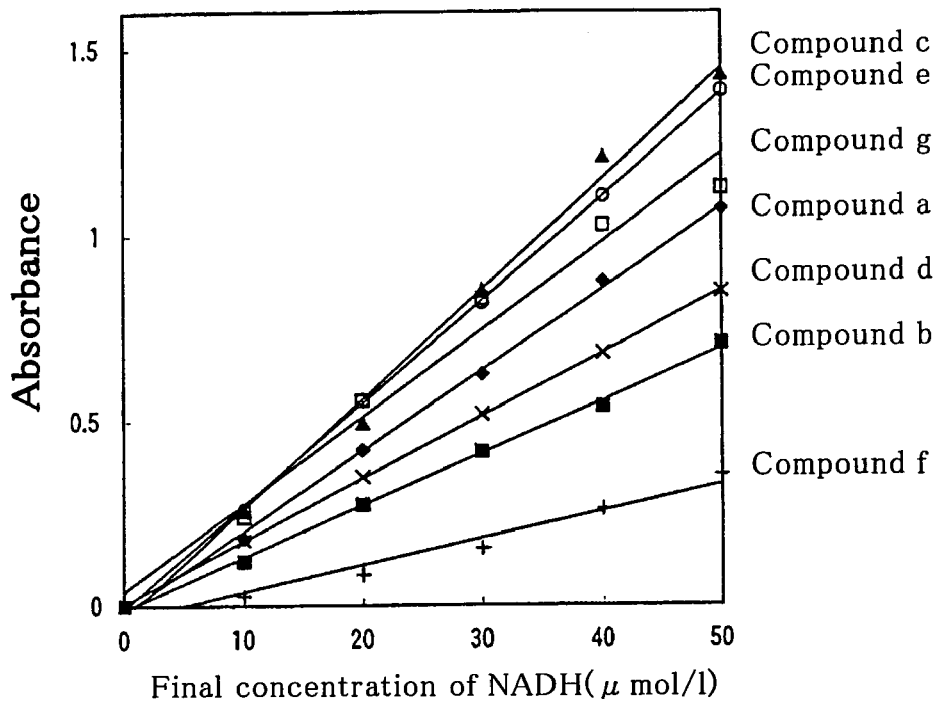
FIG. 12 shows the calibration chart of reduced form of nicotinamide adenine dinucleotide, obtained by measuring the absorption spectra.

To a solution (5 ml) of 50 mM Tris-HCl buffer (pH 8.0) containing 1 mM of compound a, b, c, d, e or f and 1-methoxy-5-methyl-phenadium methyl sulfate (hereinafter abbreviated to "1-methoxy PMS") was added 0, 10, 20, 30, 40 and 50 μl of 5 mM solution of reduced nicotinamide adenine nucleotide (hereinafter abbreviated to "NADH") so that the resultant concentration of NADH was 0, 10, 20, 30, 40 or 50 μmol/l, respectively. The absorbance of each solution was measured after the reaction for 5 minutes at room temperature. The absorption spectra thus obtained of the compounds are shown in FIG. 5 (compound a), FIG. 6 (compound b), FIG. 7 (compound c), FIG. 8 (compound d), FIG. 9 (compound e), FIG. 10 (compound f) and FIG. 11 (compound g). With increasing NADH concentration, the absorbance at 527 nm for compound a, 493 nm for compound b, 472 nm for compound c, 530 nm for compound d, 474 nm for compound e, 530 nm for compound f and 473 nm for compound g increased, evidencing the formation of the formazans. No stains on the cuvette with the formazans were observed. As shown in FIG. 12, the relationship between the NADH concentration and the absorbance gives a calibration chart with good linearity, verifying that the compound of the present invention can be used to the quantitative analysis of the dehydroganase reaction.

EXAMPLE 4

Figure 13:
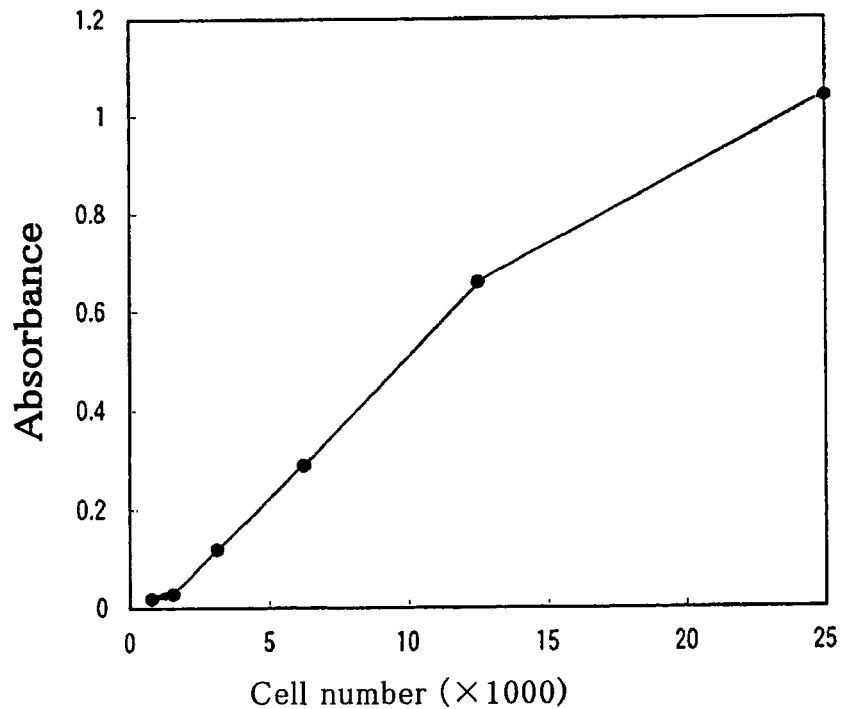
FIG. 13 shows the relationship between the number of cells and the absorbance.

A reagent solution was prepared by dissolving the compound d (5 mM) and 1-methoxy PMS (0.2 mM) in 150 mM NaCl solution. Human uterine cervix cancer cells were seeded (100 μl for each well) on a 96-well microplate by twofold dilution method starting with 25000 cells/well and incubated at 37° C. for 3 hours in a cell culture incubator. 10 μl of the reagent solution was added on each well. The absorbance of the solutions in each well at 530 nm was recorded with a microplate reader after incubating at 37° C. for 1.5 hours. No stains on the microplate with the formazans were observed. There was obtained a good calibration chart between the number of cells (which corresponds to the concentration of enzyme or substrate thereof) and the absorbance (FIG. 13).

INDUSTRIAL APPLICABILITY

The present invention can be applied as a clinical test method wherein a stable reagent with long life is utilized to obtain meaningful information for clinical diagnosis or treatment by quantitative analysis of the activities of various dehydrogenases in biological systems. Moreover, the present invention is also useful for the development of new chemicals and medicines as a method for ascertaining their toxicities or efficacious effects, by measuring the activities of dehydrogenases in cultured cells or leaked out of cells.

The invention claimed is:

1. A water soluble tetrazolium compound expressed by the following general formula (1):

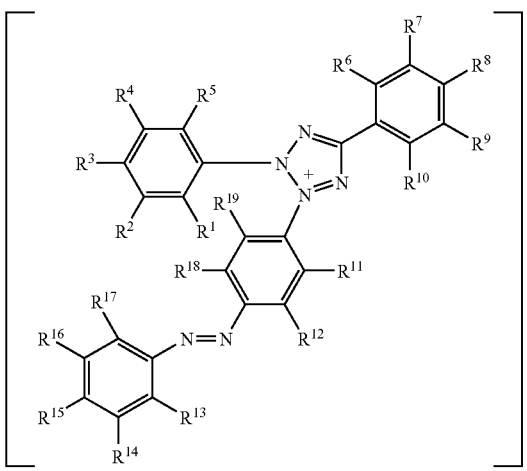

(1)

wherein each of $R^1$ to $R^{19}$ independently represents hydrogen atom; nitro group; sulfonate group; or alkyl, alkoxy, sulfoalkyl or sulfoalkyloxy groups having 1 to 4 carbon atoms; provided that each of at least two of $R^1$ to $R^{19}$ independently represents sulfonate group; or sulfoalkyl or sulfoalkyloxy groups having 1 to 4 carbon atoms; and M represents an alkali metal or ammonium ion.

2. A process for a quantitative analysis of dehydrogenase or substrate thereof, in which a tetrazolium compound of claim 1 is utilized.

3. The process of claim 2, in which the activity of the dehydrogenase present in cultured cells is measured.

4. The process of claim 2, in which the activity of the dehydrogenase leaked out of cells is measured.

* * * * *